(12) United States Patent
Lopatin

(10) Patent No.: US 7,926,356 B1
(45) Date of Patent: Apr. 19, 2011

(54) APPARATUS FOR MEASURING THE HEALTH OF SOLID ROCKET PROPELLANT USING AN EMBEDDED SENSOR

(75) Inventor: Craig M. Lopatin, Washington, DC (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 1027 days.

(21) Appl. No.: 11/801,772

(22) Filed: Apr. 26, 2007

(51) Int. Cl.
*G01B 7/16* (2006.01)
(52) U.S. Cl. .......................................... 73/768; 73/767
(58) Field of Classification Search .................... 73/768, 73/775, 767, 802, 803; 324/681
See application file for complete search history.

(56) References Cited

U.S. PATENT DOCUMENTS

| | | | |
|---|---|---|---|
| 3,395,564 A * | 8/1968 | Rastrelli et al. .................. | 73/768 |
| 3,937,070 A * | 2/1976 | Briar ................................ | 73/768 |
| 4,074,563 A * | 2/1978 | Briar et al. ................. | 73/112.01 |
| 4,567,769 A | 2/1986 | Barkhoudarian | |
| 5,038,295 A | 8/1991 | Husband et al. | |
| 5,387,095 A | 2/1995 | Mahoney et al. | |
| 6,006,163 A | 12/1999 | Lichtenwalner et al. | |
| 6,214,137 B1 | 4/2001 | Lee et al. | |
| 7,581,450 B2 * | 9/2009 | Johnson et al. .................. | 73/768 |

OTHER PUBLICATIONS

Piezo Film Sensors Technical Manual, published by Measurement Specialties, Inc., Sensor Products Division, 950 Forge Avenue, Norristown, PA 19403 (Apr. 2, 1999). p 56.
"Sensitivity of piezo wafers to the curing of thermoset resins and thermoset composites", Xiaoming Wang et al., Smart Materials and Structures 7 p. 113 (1998).

* cited by examiner

*Primary Examiner* — Lisa M Caputo
*Assistant Examiner* — Punam Roy
(74) *Attorney, Agent, or Firm* — Fredric J. Zimmerman

(57) ABSTRACT

An invented apparatus for nondestructively remotely measuring the health of an energetic material, includes a piezoelectric capacitance sensor having an exterior surface that is substantially inert to the energetic material. The piezoelectric capacitance sensor provides an analog signal that is commensurately responsive to the modulus of material in intimate contact with the sensor. The apparatus also includes an interrogator for interrogating the sensor as to a capacitance of the piezoelectric capacitance sensor. The interrogator converts the analog signal of the capacitance into a digital representation. The apparatus further includes a means of communicating the digital representation to a remote communication device.

20 Claims, 3 Drawing Sheets

APPARATUS FOR MEASURING THE HEALTH OF SOLID ROCKET PROPELLANT USING AN EMBEDDED SENSOR

STATEMENT OF GOVERNMENT INTEREST

The invention described herein may be manufactured and used by or for the Government of the United States of America for Governmental purposes without the payment of any royalties thereon or therefore.

BACKGROUND OF THE INVENTION

1. Field of the Invention

The present invention relates generally to sensors, and in particular to a nondestructive method of utilizing piezoelectric sensors to determine in situ the health of solid rocket propellants.

2. Related Art

There is a need for an apparatus for measuring the health of solid rocket propellant using an embedded sensor for self-sensing ordnance. The need is particularly acute with regard to solid rocket motors, since it is known that aging of propellant can lead to significant degradation in weapon performance and, possibly, catastrophic failure. The need correlates with the military requirements that mandate future tactical missiles be kept for extended periods of time on board ship, without periodic, land-based inspections. A particularly facile method of inspection would be one where the solid rocket missiles have a solid rocket motor with a propellant that has a method of self-sensing the health of the propellant.

Classical approaches used to predict and detect material degradation have been to develop aging models for predicting the state of a material, given an assumed or measured environmental history, and the use of non-destructive testing methods such as ultrasound and X-rays. Both approaches, as currently practiced, are inadequate to meet the needs of a real-time, self-sensing health monitoring system. Thus, in recent years efforts have been devoted to investigate an entirely new approach to meet the goal of self-sensing ordnance—the use of embedded sensors.

The use of embedded sensors is potentially a better analytical technique for several reasons. A sensor embedded in the propellant inside a weapon, versus an external technique that is obstructed by a thick metallic housing, is in direct contact with the energetic material, and thus in a better position to detect subtle changes in properties. An embedded sensor is always present in the weapon, and thus the weapon's health can always be queried, thus meeting the goal of making the ordnance self-sensing.

Several types of embedded sensors are being investigated in the solid rocket motor community. Bond line sensors are small pressure sensors used to measure the stress between the propellant and case. The sensors are used to detect the perturbation in the stress field due to the presence of damage. Difficulties with this method are as follows. The bond line sensor requires sophisticated finite element modeling and analysis to characterize the damage from the measured signals. The analysis is further complicated by the unknown change in material properties due to aging, leading to problems in data interpretation. Bond line sensors are difficult to install, as they need to be cast into the rocket motor, and they have relatively high cost, on the order of $250 per sensor. A second type of sensor is an optical fiber strain sensor. Optical fiber strain sensors are used in a similar manner to bond line sensors, in that they detect changes in the strain field due to the presence of damage. While optical fiber sensors can be placed in the bore, and thus can be installed after the motor is cast, the difficulty in interpreting the signals is a significant challenge.

A weakness with both these sensors is that they do not provide an unambiguous indication of the system's health, and significant analysis is needed to interpret the results.

What is needed is a reliable measure of the health of the solid rocket propellant through the use of an embedded sensor, where the method provides an unambiguous measure of material state, where the method employs an embedded sensor that is relatively inexpensive.

SUMMARY OF THE INVENTION

The invention is an apparatus, and related method, for determining the health of solid rocket propellants using an embedded piezoelectric capacitance sensor. In contrast to prior structures using in situ sensors, which provide a measure of only the stress or only strain, the invention measures the modulus at potentially multiple locations. By measuring the modulus at multiple locations using multiple sensors one can determine gradients in modulus. The measurements can be made using a single integrated circuit interrogator, which has the capability of determining the capacitance of multiple sensors. The capacitance of the sensors is then correlated to a modulus. Both ceramic and polymeric film piezoelectric sensors have a reduction in capacitance as material in intimate contact with the sensor stiffens (e.g. the modulus increases). The ceramic piezoelectric sensors are generally comprised of lead zirconate titanate (PZT). Piezoceramics are very efficient, and are thermally stable, but have a poor mechanical impedance match to propellant and are brittle. The polymeric sensor may be comprised of PVDF (polyvinylidene fluoride) or copolymers thereof. The PVDF piezoelectric sensors generally have a film of PVDF that is formed by stretching it below the melting point of the PVDF. The stretching may be performed in the presence of a very high electric field thereby imparting crystallinity, and highly orienting the C-F polymeric material under the influence of the electric field. The PVDF film often has an electrically conductive coating on one or both sides, where the conductive coating is for example selected from silver, nickel, aluminum, copper, gold, or other conductive alloys. The PVDF crystalline film is a piezoelectric material and a dielectric material that is excellent for forming capacitors. While the piezoelectric polymer has a better impedance match with propellant, and has the advantage of being flexible, it has the weakness of relatively poor thermal stability, and therefore is unsuitable if during the embedding process, the molten cast propellant is hot, as the heat can have a deleterious effect on the polymer (i.e. the polymer relaxes). It should be noted that measuring the electrical impedance of the sensor is also of use, and the word "capacitance" is used to refer to electrical impedance.

The apparatus for nondestructively remotely measuring the health of an energetic material, includes a piezoelectric capacitance sensor having an exterior surface that is substantially inert to the energetic material. The piezoelectric capacitance sensor provides an analog signal that is commensurately responsive to the modulus of material in intimate contact with the sensor. The apparatus also includes an interrogator for interrogating the sensor as to a capacitance of the piezoelectric capacitance sensor. The interrogator converts the analog signal of the capacitance into a digital representation. The apparatus further includes a means of communicating the digital representation to a remote communication device.

DETAILED DESCRIPTION

Figure 1:
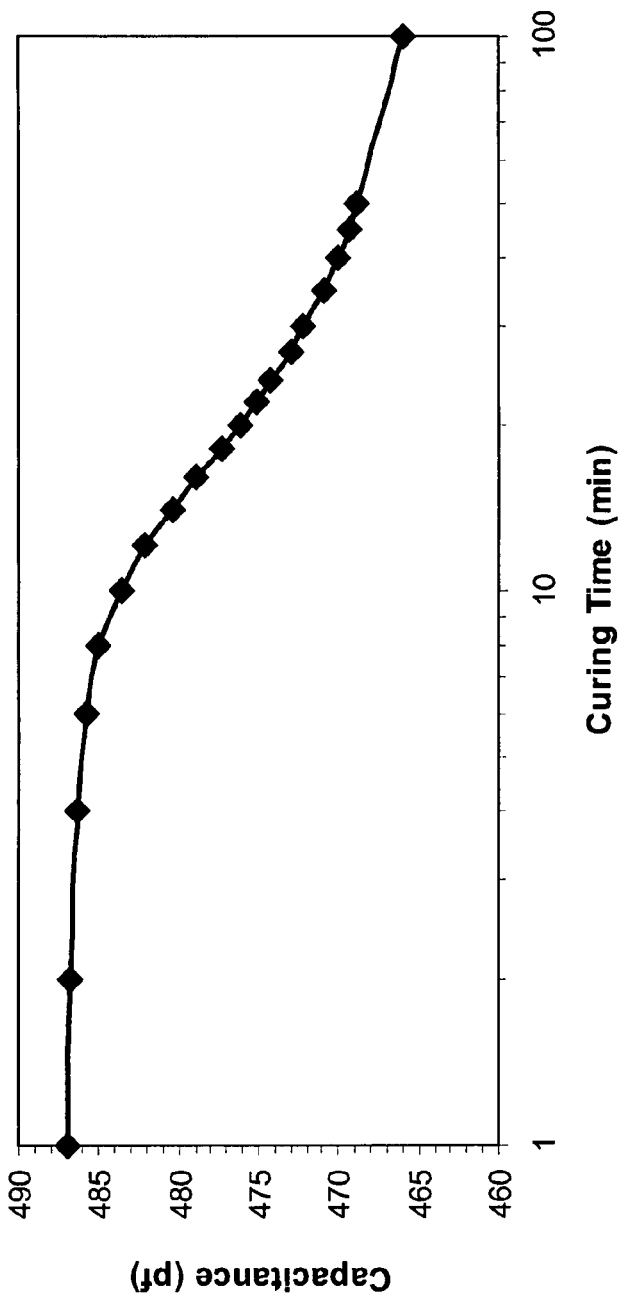
FIG. 1 is a graph of the capacitance versus cure time for a resin as it stiffens, increasing in modulus, using a PVDF sensor.

The invention is an apparatus, and a related method, for nondestructively remotely measuring the health of an energetic material, where the energetic material is a solid rocket propellant. The invented apparatus recognizes that as propellants and the like develop health issues, the materials become harder (i.e. shear modulus increases), and there can be propellant/insulater debonding and bore cracking. Cracks and debonding can induce failure of the rocket upon ignition. In addition, some propellants may become softer with age, leading to "slump"—unacceptable permananet deformation of the propellant. Motors are chemically active throughout their entire lives, leading to issues of motor aging perhaps far down the road. A major cause of hardening in propellants over time is oxidative cross-linking. The introduction of moisture into the system may also be extremely destructive to material properties in both the bulk materials and at the interfaces. There are two general classes of flaws in the PLI system. The first is a void or inclusion, generally located in the bulk propellant. The second is a fracture or debond. Voids in propellant often occur as a result of insufficient settling of the propellant during the casting process. Trapped air bubbles are not fully eliminated and small voids are formed which contain no propellant. If small enough, these small voids are not generally of great concern. However, if the voids are proximate to an interface or other high stress or strain region, then these small voids may contribute to the formation of cracks. Inclusions are objects that inappropriately end up in the propellant. Inclusions may be large pieces of propellant ingredients or other motor materials, but also include anomalous objects. Notable inclusions that have appeared in motors include lead shot, a crumpled paper cup, and a wrench. Regardless of the source, these objects are often poorly bonded to the propellant and cause perturbations to the stress/strain field of the motor in a similar fashion as voids. If the item is large enough or is likely not to be fully consumed in the motor, then the item can damage the housing and the nozzle. Depending on the composition of the inclusion, the combustion process in the region can be significantly changed. In some cases, materials such as fine metal wires are placed in the propellant to increase the burning rate by augmenting thermal conduction and providing a flame path.

Cracks can occur throughout the motor, although they are often seen in the bore, particularly in motors that have undergone thermal cycling. When a crack occurs, there are two scenarios. In the first case, when the combustion surface reaches the crack, the flame speed exceeds the crack propagation velocity. In this situation, the crack tip is blunted by the burning and does not propagate, so the concern is simply the increase in pressure of the motor due to additional burning surface area. If the crack area is small compared to the surface area of the motor, the pressure will not be significantly increased and this will not a major issue. In the case that the crack propagation speed is greater than that of the flame, the crack will propagate. In this situation, burning surface is exposed deeper in the motor before it was expected. Since the insulation thickness is determined by the time of exposure to the hot gases (with an appropriate factor of safety), early exposure can overwhelm the insulation, heating the housing and creating an opportunity for failure. Cracks also occur in the propellant near the propellant-liner interface. These cracks compound the problem, as not only is there hot gas near the wall, but if the crack propagates, it detaches the motor grain from the bonding surface. Debonds are similar to the cracks described above, but result from insufficient or incomplete bonding between two of the propellant-liner-insulator materials. As with cracks, the concerns are augmented burning near the housing wall and the structural impact of the decreased bonding.

In any case, the degree of degradation in the propellant can be detected by a change in capacitance, as the previously enumerated symptoms are generally manifestations of stress failure as a consequence of changes in the shear modulus. FIG. 1 illustrates the capability of PVDF piezoelectric sensor to detect an increase in stiffness. As the surrounding material becomes stiffens with time, there is a decrease in capacitance. In the illustration, the increase in stiffness (i.e. modulus) is due to cross-linking, and is a illustrative of the measurement capabilities of piezoelectric sensors. The historical data and auxiliary test data, such as X-ray data should be factored into the installation of the embedded sensors.

Deciding on the position of the sensors depends on whether they will be used mainly for determination of modulus or damage. The two typically correlate, but can vary in degree. If the primary use is to determine modulus, then the sensors are placed in a low stress area, so that it will be unlikely that the volume of material surrounding the sensor will contain damage. Example areas would be in locations far from the bulb tip stress reliefs. If the primary use will be to determine whether damage is present (damaged material also can be considered as "less stiff material"), than the sensors should be placed near areas where damage is expected to occur, such as near bulb tip stress reliefs and the propellant-liner interface.

Monolithic sensors can be used to generate both normal and tangential motion. A sensor with a composite construction also allows both types. As propellants are very energetic materials, the piezoelectric sensor is selected to develop very little heat to minimize the possibility of accidental ignition. A rough order of magnitude calculation shows that the temperature rise due to powering the sensor is minimal. Assume that the area of sensor is 1 $mm^2$, the capacitance of sensor is 0.32 nf, the excitation voltage is 10 mv, the frequency of excitation is 32 KHz, the volume of material surrounding sensor is $10^{-3}$ cm having a mass of 1 mg, and heat capacity of propellant of 0.5 cal/g °C.; then the power dissipated by the sensor is about 0.2 microwatt, and the temperature rise in the propellant surrounding the sensor would thus be about $3 \times 10^{-5}$ ° C./sec. This temperature is within a large margin of safety.

The invented apparatus, and related method further discloses how energy is provided for the sensor and the support electrical components. The apparatus also discloses how capacitance is measured, and how the measured capacitance is communicated from the embedded sensor to a monitoring system, such as ATOS, which is an advanced technology ordnance surveillance system.

Figure 2:
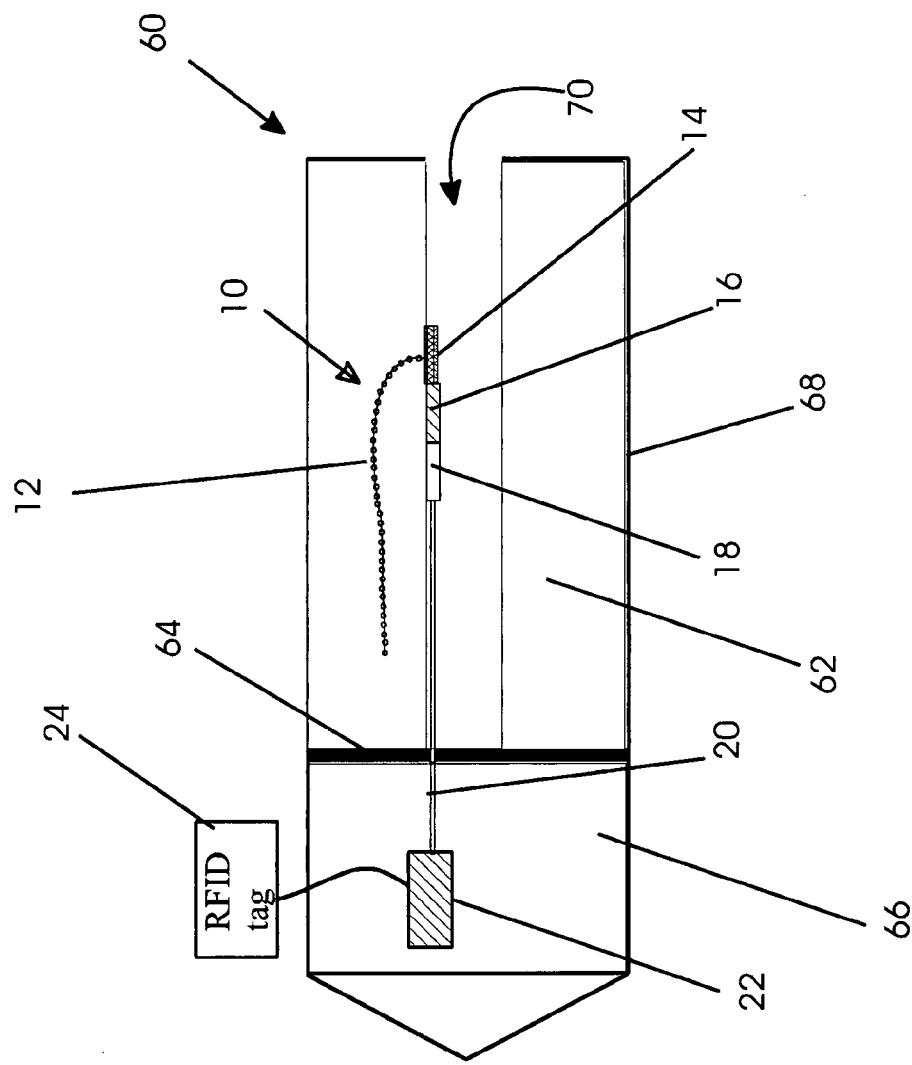
FIG. 2 is a diagrammatic view of solid rocket propellant motor having a plurality of embedded piezoelectric sensors in communication with an interrogator, where power and query command is housed in the guidance section of the rocket.

The invented apparatus, and related method for measuring the health of a solid rocket propellant, includes embedding at least one piezoelectric capacitance sensor in the propellant, where the capacitance of the sensor is a function of a modulus of the propellant, and where the position is determined by the previously enumerated considerations. The sensor's capacitance is measured at a predetermined frequency. The capacitance of the piezoelectric capacitance sensor is converted into a digital representation which is communicated to a remote device that converts the digital representation to a modulus or gradient in modulus (when multiple sensors are used). In subsequent analysis, the modulus (or gradient in modulus) is correlated to the health of the solid rocket propellant. The piezoelectric capacitance sensor includes one sensor or a plurality of sensors embedded in the energetic material, where individual sensors can be queried. As illustrated in FIG. 2, the sensors 12 are electrically attached to an integrated circuit 10, where the integrated circuit 10 is in communication with a microcontroller 14, which records and processes the information. The sensors 12 as illustrated are embedded in the propellant 62 of rocket 60 having a motor 68 and a guidance section 66. The motor 68 is separated from the guidance section 66 by bulkhead 64. A thick metallic housing 68 encases the propellant 62, which has a substantially annular burning bore 70.

Examples of a microcontroller 14 are a single chip capacitance analog to digital converters (sometimes referred to as "interrogators" 14) with a single input, such as, AD7745, or a dual input chip, such as, AD7746, which are products of Analog Devices, Inc. AD7745/AD7746 are high resolution, $\Sigma$-$\Delta$ capacitance-to-digital converters (CDC). The capacitance may be measured by directly connecting the interrogator 14 to a sensor 12. The CDC architecture features inherent high resolution (24-bit no missing codes, up to 21-bit effective resolution), high linearity (±0.01%), and high accuracy. The capacitance input range is ±4 pF changing), while it can accept up to 17 pF common-mode capacitance not changing), which can be balanced by a programmable on-chip, digital-to-capacitance converter (CAPDAC). The AD7745 chip has one capacitance input channel, while the AD7746 chip has two channels. Each channel can be configured as single-ended or differential. The CDCs interrogators are designed for floating capacitive sensors. The chips have an on-chip temperature sensor with a resolution of 0.1° C. and accuracy of ±2° C. The chips also have an on-chip voltage reference and an on-chip clock generator, and these eliminate the need for any external components in capacitive sensor applications. The chips have a standard voltage input, which together with the differential reference input allows easy interface to an external temperature sensor, such as an RTD, a thermistor, or a diode. The CDCs can operate with a single power supply from 2.7 V to 5.25 V. Alternatively, a series of sensors can be interrogated using a CDC such as AD7142, which can sample up to 14 sensors. The AD7142, which is also a product of Analog Devices, Inc, is an integrated capacitance-to-digital converter with on-chip environmental calibration for use in systems requiring a novel user input method. Although the sensor excitation frequency of the AD7142 is fixed, the resonance frequency of the sensors may be tailored to match this frequency, if necessary. The AD7142 CDC has 14 inputs channeled through a switch matrix to a 16-bit, 250 kHz sigma-delta ($\Sigma$-$\Delta$) capacitance-to-digital converter. The CDC is capable of sensing changes in the capacitance of the external sensors and uses this information to register a sensor activation. The AD7142 has on-chip calibration logic to account for changes in the ambient environment. Another integrated circuit interrogator is the AD5933, which measures the electrical impedance of the sensor, thus providing phase information in addition to capacitance. An alternative method for measuring capacitance includes placing each sensor in a voltage divider configuration with a fixed resistor. Measuring the voltage across the resistor to provide a measure of both the capacitance (through the impedance-capacitance relationship for a capacitor) and the current through the sensor. Accordingly, the current-voltage relationship may be obtained and of use.

As illustrated in FIG. 2 the interrogator 14 is in communication with a digital to optical converter 16, which generally includes a microcontroller. The digital to optical converter 16 converts the digital representation into an optical signal which is transmitted through a fiber optic cable 20 to a optical to digital converter 22 located in the guidance section 66 of the rocket 60. Information is uploaded to an RFID device 24, which is a scannable member of ATOS (advanced technology ordnance surveillance system). As illustrated in FIG. 2, the optical fiber 20 can additionally provide a non-electrical means of transmitting power through the innards of the rocket motor 68. The optical to digital converter 22 can send enough light power through the optical fiber 20 to power the digital to optical converter 16 and the CDC interrogator 14. The optical fiber 20 interfaces an optical to voltage converter 18.

The apparatus can employ a piezoelectric capacitance sensor, selected from the group consisting of a piezoceramic sensor or a piezoelectric polymer sensor. Generally, the piezoelectric polymer sensor is comprised of piezoelectric PVDF polymer, copolymer, or a combination thereof. Generally, the piezoceramic sensor is comprised of lead zirconate titanate.

Figure 3:
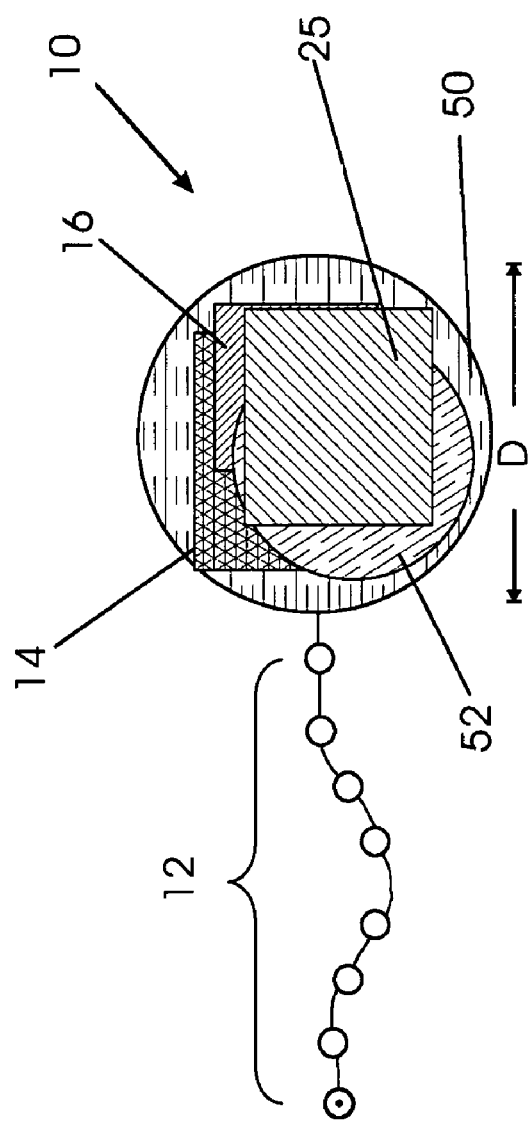
FIG. 3 a diagrammatic view of a pill-sized unit that has self-contained interrogation and communication electronics, where the unit has at least one integral piezoelectric sensor, and can be embedded during the casting of the propellant.

FIG. 3 illustrates a diagrammatic view of a pill-sized unit that has self-contained interrogation and communication electronic components, where the unit has at least one integral piezoelectric sensor, and can be embedded during the casting of the propellant. In the invented method, the embedded sensor apparatus 10 includes a series of sensors 12, which interface an RF communication component 25 housed in a protective can 50. The size of the pill-sized unit may be on the order of about 2 mm-20 mm, and more particularly, about 5 mm. The pill-sized unit contains the CDC 14, such as the AD7142 previously discussed; a low power microcontroller 16, such as 8051F300 (e.g. 8051); a battery 52; and the RF communication chip 25, such as SX1223. SX1223 is a product of Semtech. The SX1223 is a single chip transmitter operating in the UHF frequency bands including the 434, 869 and 915 MHz license-free ISM (Industry Scientific and Medical) bands. Its highly integrated architecture allows for minimum external components while maintaining design flexibility. All major RF communication parameters are programmable and most of them can be set dynamically. The SX1223 offers the advantage of high data rate communication at rates of up to 153.6 kbit/s. The SX1223 is optimized for low cost applications while offering high RF output power.

The apparatus, and related method for nondestructively remotely measuring the health of propellant in a solid rocket motor, includes the steps of providing an electronically integrated combination of piezoelectric capacitive sensors and communication components in a self contained, pill-sized unit, where the sensors are in electrical communication through a protective housing with the communication components. The communication components include a capacitance to digital converter; a low power microcontroller; an RF communication chip; and a battery. The method further includes positioning the self contained, pill-sized unit in a mold for the solid rocket propellant; and casting the solid rocket propellant. The process further consists of periodically measuring the capacitance of each of the piezoelectric capacitance sensors; converting the measurement of the capacitance into a digital representation; communicating the digital representation to a remote device; relating the digital representation to modulus (or gradient modulus); and correlating the modulus (or gradient modulus) to the health of the propellant. The communication of queries, in an exemplary embodiment, is effected via an RF communication chip, which is a member of an advanced technology ordnance surveillance system (ATOS). A stated purpose of the ATOS is to locate and monitor the health of munitions.

To facilitate exact positioning of the sensors, the rocket motor casing can be pre-fitted with scaffolding that holds the sensors prior to casting the propellant. This method includes providing a rocket motor housing with a scaffolding; attaching at least one piezoelectric capacitance sensor to the scaffolding; casting the propellant, therein forming a rocket motor with an annular bore 70, where the rocket motor has at least one piezoelectric capacitance sensor embedded in solidified propellant; connecting at least one piezoelectric capacitance sensor to a capacitance to digital converter, such as an interrogator positioned near the annular bore of the motor; interfacing a microcontroller having a digital to optical converter with the capacitance to digital converter and with an optical fiber, where the optical fiber provides both communication and power; extending a length of the optical fiber through the annular bore into the guidance section of the rocket; and interfacing the optical fiber to a communication device. In an exemplary embodiment, the communication device is an active RFID, which is a scannable member of the advanced technology ordnance surveillance system. In an exemplary embodiment, the scaffolding is a compliant material (e.g. rubber), and has the capability of attaching and positioning multiple sensors. The capacitance of individual sensors can be queried using an interrogator.

Another structure, and related method of installing the health monitoring system, is by simply dropping the "pill" into the motor as it is being cast. The position can later be determined using X-rays.

It is to be understood that the foregoing description and specific embodiments are merely illustrative of the best mode of the invention and the principles thereof, and that various modifications and additions may be made to the invention by those skilled in the art, without departing from the spirit and scope of this invention, which is therefore understood to be limited only by the scope of the appended claims.

Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should at least be construed in light of the number of significant digits and by applying ordinary rounding.

What I claim is:

1. An apparatus for nondestructively remotely measuring the health of an energetic material, comprising:
    a piezoelectric capacitance sensor having an exterior surface that is substantially inert to the energetic material, said piezoelectric capacitance sensor providing an analog signal that is commensurately responsive to the modulus of material in intimate contact with the sensor;
    an interrogator for interrogating the sensor as to a capacitance of the piezoelectric capacitance sensor;
    the interrogator for converting the analog signal of the capacitance into a digital representation; and
    a means of communicating the digital representation to a remote communication device,
    wherein said apparatus further comprises a consumable scaffolding to, pre-position at least one piezoelectric capacitance sensor.

2. The apparatus according to claim 1, further comprising an algorithm relating the digital representation to one of a modulus and a gradient in modulus.

3. The apparatus according to claim 2, further comprising a paradigm that correlates said one of said modulus and said gradient in modulus to the health of the energetic material.

4. The apparatus according to claim 1, wherein said piezoelectric capacitance sensor is one of a piezoceramic sensor and a piezoelectric polymer sensor.

5. The apparatus according to claim 4, wherein said piezoelectric polymer sensor is comprised of at least one of piezoelectric PVDF polymer, and a copolymer.

6. The apparatus according to claim 4, wherein said piezoceramic sensor is comprised of lead zirconate titanate.

7. The apparatus according to claim 1, wherein said interrogator provides a frequency and a voltage to the sensor.

8. The apparatus according to claim 7, wherein said frequency is less than 100 KHz, and the voltage is less than 1 volt.

9. The apparatus according to claim 1, wherein said communicating means is selected from at least one of a component with an RF communication chip, a component that transmits and receives an optical transmission, a component that communicates through an optical fiber, a component that is an active RFID device, and a combination of communication components.

10. The apparatus according to claim 1, wherein said apparatus further comprises a battery.

11. The apparatus according to claim 10, wherein said apparatus further comprises a protective can.

12. The apparatus according to claim 1, wherein said apparatus further comprises a means of communicating to an advanced technology ordnance surveillance system (ATOS).

13. An apparatus for nondestructively remotely measuring the health of a solid rocket propellant, comprising:
    a plurality of piezoelectric capacitance sensors;
    an interrogator comprising a capacitance to digital converter, and a low power micro-controller;
    a means of communicating with a remote device;
    a battery; and
    a pill-sized unit housing for the interrogator, the communicating means and the battery,
        wherein the apparatus is robust and suitable for embedding in the solid rocket propellant at a time it is cast.

14. The apparatus according to claim 13, wherein said interrogator provides a frequency and a voltage to each of the plurality of piezoelectric capacitance sensors.

15. The apparatus according to claim 13, wherein said communicating means comprises a RF communication chip.

16. The apparatus according to claim 13, wherein each of said plurality of piezoelectric capacitance sensors provides an analog signal that is commensurately responsive to a modulus of material in intimate contact with said each of said plurality of piezoelectric capacitance sensors.

17. The apparatus according to claim 13, wherein the interrogator converts individual analog signals of capacitance of each of the piezoelectric capacitance sensors into a digital representation.

18. The apparatus according to claim 17, further comprising an algorithm relating the digital representation to one of a modulus and a gradient in modulus.

19. The apparatus according to claim 18, further comprising a paradigm for correlating said one of said modulus and said gradient in modulus to the health of the energetic material.

20. An apparatus for nondestructively remotely measuring the health of a solid rocket propellant, comprising:
- a plurality of piezoelectric capacitance sensors;
- an interrogator comprising a capacitance to digital converter, and a low power micro-controller;
- a means of communicating with a remote device;
- a battery; and
- a housing for the interrogator, the communicating means and the battery,
    - wherein the apparatus is robust and suitable for embedding in the solid rocket propellant at a time it is cast.

* * * * *